(12) United States Patent
Cai et al.

(10) Patent No.: US 6,369,298 B1
(45) Date of Patent: Apr. 9, 2002

(54) AGROBACTERIUM MEDIATED TRANSFORMATION OF SORGHUM

(75) Inventors: Tishu Cai, Ellisville, MO (US); Dorothy A. Pierce, Urbandale, IA (US); Laura A. Tagliani, Zionsville, IN (US); Zuo-Yu Zhao, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/056,418

(22) Filed: Apr. 7, 1998

Related U.S. Application Data
(60) Provisional application No. 60/045,121, filed on Apr. 30, 1997.

(51) Int. Cl.$^7$ ............................. A01H 1/00; A01H 5/00; C12N 5/04; C12N 5/10; C12N 15/84
(52) U.S. Cl. ................... 800/294; 435/419; 435/430.1; 435/469; 800/320
(58) Field of Search .......................... 435/320.1, 430.1, 435/469, 419; 800/294, 320

(56) References Cited

U.S. PATENT DOCUMENTS

| 5,591,616 A | 1/1997 | Hiei et al. ................ 435/172.3 |

FOREIGN PATENT DOCUMENTS

| EP | 0 604 662 A1 | 6/1993 | ............ A01H/1/00 |
| EP | 0 672 752 A1 | 1/1994 | ............ C12N/15/00 |
| EP | 0 586 355 A2 | 3/1994 | |
| EP | 0 687 730 A1 | 6/1994 | ............ C12N/15/00 |
| EP | 0 604 662 A1 | 7/1994 | |
| EP | 0 672 752 A1 | 9/1995 | |
| EP | 0 687 730 A1 | 12/1995 | |
| EP | 0 709 462 A2 | 1/1996 | ............ C12N/15/82 |

OTHER PUBLICATIONS

Ko, et al, "In Vitro" May 20–24, 1995, Congress on In Vitro Biology Denver Co., vol. 31, No. 3, Pt2, 71A.*
Vain, P., et al., "Foreign Gene Delivery into Monocotyledonous Species", *Biotechnology Advances*, 13 (4):653–671 (1995).
Casas, et al., "Transgenic Sorghum Plants Via Microprojectile Bombardment", *Proc. Natl. Acad. Sci. USA*, 90:11212–11216 (1993).

Safaraliev, et al., "Preparation and Properties of Polycrystalline SiC–AIN Solid Solutions", *Semiconductors*, 27(3):224–227 (1993).
Weeks et al., "Rapid Production of Multiple Independent Lines of Fertile Transgenic Wheat (*Triticum aestivum*)", *Plant Physiol.*, 102:1077–1084 (1993).
Christou et al., "The Impact of Selection Parameters on the Phenotype and Genotype of Transgenic Rice Callus and Plants", *Transgenic Research* 4:44–51 (1995).
Wilson et al., *Maize*, pp. 65–80 (1995).
Godwin et al., "Transgenic Grain Sorghum (*Sorghum bicolor*) Plants Via Agrobacterium", *Improvement of Cereal Quality by Genetic Engineering*, pp. 47–53 (1994).
McElroy et al., "Foreign Gene Expression in Transgenic Cereals", *TIBTECH*, 12:62–68 (1994).
Ishida et al., "High Efficiency Transformation of Maize (*Zea mays* L.) Mediated by *Agrobacterium tumefaciens*", *Nature Biotechnology*, 14:745–750 (1996).
Casas et al., "Transgenic Sorghum Plants Via Microprojectile Bombardment", *Proc. Natl. Acad. Sci. USA*, 90:11212–11216 (1993).
Kononowicz et al., "New Vistas Are Opened for Sorghum Improvement by Genetic Transformation", *African Crop Science Journal*, vol. 3, No. 2:171–180 (1995).
Casas et al., "Cereal Transformation Through Particle Bombardment", *Plant Breeding Reviews*, 13:235–264 (1995).
Walden et al., "Gene–Transfer and Plant–Regeneration Techniques", *TIBTECH*, 13:324–331 (1995).

\* cited by examiner

*Primary Examiner*—Elizabeth F. McElwain
*Assistant Examiner*—Cynthia Collins
(74) *Attorney, Agent, or Firm*—Pioneer Hi-Bred International, Inc.

(57) ABSTRACT

Methods and compositions for the efficient transformation of sorghum is provided. The method involves infection with Agrobacterium, particularly those comprising a super-binary vector. In this manner, any gene of interest can be introduced into the sorghum plant. The transformed gene will be flanked by at least one T-DNA border and present in the transformed sorghum in low copy number. Transformed sorghum, cells, tissues, plants, and seed are also provided. The invention encompasses regenerated, fertile sorghum plants, transgenic seeds produced therefrom, T1 and subsequent generations.

28 Claims, 2 Drawing Sheets

AGROBACTERIUM MEDIATED TRANSFORMATION OF SORGHUM

CROSS-REFERENCE

This application claims the benefit of U.S. Provisional Application No. 60/045,121, filed Apr. 30, 1997.

FIELD OF THE INVENTION

The invention relates to methods and compositions for the transformation of sorghum, particularly to methods for transformation utilizing Agrobacterium.

BACKGROUND OF THE INVENTION

Sorghum is one of the most important cereal crops for subsistence farmers in arid and semi-arid portions of Africa, Asia and the Americas. The crop is essential for human life on marginal lands throughout the poorest regions of the world. However, further development of the crop is needed if food production in these areas is to keep pace with increases in population. In developed countries, sorghum is important as a feed crop and as a crop that can be grown on marginal lands as part of a sustainable agroecosystem.

Sorghum is typically the cereal grown in areas where the extremes of high temperature and low soil moisture are unsuitable for maize. In 1991, sorghum was ranked fifth in production for all cereals with 58 million metric tons harvested on 45 million hectares of land. See, *Food and Agriculture Organization of the United Nations* (1992), *FAO Production Yearbook* 1991 (FAO, Rome) Volume 45. Sorghum is used primarily as livestock feed in the western hemisphere. The development of hybrid varieties of sorghum in the 1950s contributed substantially to the increase in production in the United States. Presently, sorghum ranks third among the cereals produced in the U.S. and is the preferred crop in areas of low water availability because of its yield stability under drought conditions.

Sorghum is plagued by diseases, especially in higher yielding environments. Many of the diseases are caused by highly variable pathogens. Generally, as yield potential increases, so does the proportion of the crop lost to diseases.

Until recently, genetic improvement of sorghum for agronomic and quality traits has been carried out by traditional plant breeding methods and improved cultural management practices. Advances in tissue culture and transformation technologies have resulted in the production of transgenic plants of all major cereals, including sorghum. To date, key to this transformation was the development of microprojectile bombardment devices for DNA delivery into cells. Microprojectile bombardment circumvented two major constraints of cereal transformation. These constraints are the lack of an available natural vector such as *Agrobacterium tumefaciens* and the difficulty to regenerate plants when protoplasts are used for transformation. Particle bombardment can target cells within tissues or organs that have high morphogenic potential. However, the use of microprojectile bombardment as a transformation vehicle has its drawbacks. Particularly, with bombardment several copies of the gene to be transferred are often integrated into the targeted genome. These integrated copies have often been rearranged and mutated. Furthermore, the transformation event may not be stable due to the insertion point or means still not an efficient process (Casas et al. (1993) *Proc. Natl. Acad. Sci. USA* 90:11212–11216).

Agrobacterium, a natural plant pathogen, has been widely used for the transformation of dicotyledonous plants. Agrobacterium remains the most widely used vector for transformation of dicot species. Because monocotyledonous plants are rarely natural hosts for Agrobacterium, they have not been expected to be susceptible to gene transfer mediated by the bacterium.

The advantage of the Agrobacterium-mediated gene transfer is that it offers the potential to regenerate transgenic cells at relatively high frequencies without a significant reduction in plant regeneration rates. Moreover, the process of DNA transfer to the plant genome is defined. That is, the DNA does not normally undergo any major rearrangements, and it integrates into the genome often in single or low copy numbers.

Agrobacterium-mediated transformation involves incubation of cells or tissues with the bacterium, followed by regeneration of plants from the transformed cells via a callus stage. Inoculation of explants has proven to be the most effective means of creating transgenic plants.

Early work with Agrobacterium indicated that the bacterium could transfer T-DNA to monocotyledonous hosts. However, clear evidence of T-DNA integration existed only for asparagus, and even in that case, no transformed plants were produced. Because of the recalcitrant nature of monocots to Agrobacterium infection, other methods, such as particle bombardment, were developed for the transformation of monocots. More recently, the transformation of maize and rice using Agrobacterium has been reported. See, Ishida et al. (1996) *Nature Biotechnology* 14:745–750; EPA 0672752A1; EPA 0687730A1; and U.S. Pat. No. 5,591,616. Among the factors indicated that affect the efficiency of transformation include the types and stages of maize tissues infected, the concentration of *A. tumefaciens*, compositions of the media for tissue culture, selectable marker genes, kinds of vectors and Agrobacterium strains, and the maize genotype. The researchers concluded that the main hurdle in transformation may have been the recovery of cells that acquired the T-DNA in their chromosomes. See, Ishida et al. (1996) supra.

While reports indicate that some genotypes of maize and rice can be transformed with Agrobacterium, there is no report of Agrobacterium-mediated transformation of sorghum. While transgenic sorghum plants have been reported following microprojectile bombardment, transgenic plants were obtained only at very low frequencies. Further, inherent characteristics of the sorghum cells make them somewhat unresponsive for transient expression. Casas et al. (1993) *Proc. Natl. Acad. Sci. USA* 90:11212–11216.

Accordingly, there is needed an efficient method for the transformation of sorghum wherein stable transformation of large inserts can be obtained. That is, there is needed a method for the transformation of sorghum utilizing Agrobacterium.

SUMMARY OF THE INVENTION

The present invention is drawn to methods and compositions for the efficient transformation of sorghum. The method involves the use of bacteria belonging to the genus, Agrobacterium, particularly those comprising a super-binary vector. In this manner, any gene of interest can be introduced into the sorghum plant. The transferred gene will be flanked by at least one T-DNA border and present in the transformed sorghum in low copy number.

Transformed sorghum cells, tissues, plants, and seed are also provided. Such transformed compositions are characterized by the presence of T-DNA borders and a low copy number of the transferred gene. The invention encompasses regenerated, fertile transgenic sorghum plants, transgenic seeds produced therefrom, T1 and subsequent generations.

DETAILED DESCRIPTION OF THE INVENTION

Compositions and methods for the efficient transformation of sorghum are provided. The transformed sorghum plants are characterized by containing transferred nucleic acid such as a transferred gene or genes of interest flanked by at least one T-DNA border inserted within the genome of the sorghum plants. The plants are normal in morphology and fertile. Generally, the transformed plants contain a single copy of the transferred nucleic acid with no notable rearrangements. Alternatively, the transferred nucleic acid of interest is present in the transformed sorghum in low copy numbers. By low copy number is intended that transformants comprise no more than five (5) copies of the transferred nucleic acid, preferably, no more than three (3) copies of the transferred nucleic acid, more preferably, fewer than three (3) copies of the transferred nucleic acid. The transferred nucleic acid will comprise at least one T-DNA border sequence.

The methods of the invention rely upon the use of Agrobacterium-mediated gene transfer. Agrobacterium-mediated gene transfer exploits the natural ability of *Agrobacterium tumefaciens* to transfer DNA into plant chromosomes. Agrobacterium is a plant pathogen that transfers a set of genes encoded in a region called T-DNA of the Ti plasmid into plant cells at wound sites. The typical result of gene transfer is a tumorous growth called a crown gall in which the T-DNA is stably integrated into a host chromosome. The ability to cause crown gall disease can be removed by deletion of the genes in the T-DNA without loss of DNA transfer and integration. The DNA to be transferred is attached to border sequences that define the end points of an integrated T-DNA.

Gene transfer by means of engineered Agrobacterium strains has become routine for most dicotyledonous plants and for some monocotyledonous plants. However, there are no reports to date of producing transformed sorghum by means of Agrobacterium-mediated transformation. See, for example, Fraley et al. (1983) *Proc. Natl. Acad. Sci. USA* 80:4803; Watson et al. (1985) *EMBO J* 4:277; Horsch et al. (1985) *Science* 227:1229; Hernalsteens et al. (1984) *EMBO J* 3:3039; Comai et al. (1984) *Nature* (London) 317:741; Shah et al. (1986) *Science* 233:478; Bytebier et al. (1987) *Pro. Natl. Acad. Sci. USA* 84:5345; Schafew et al. (1987) *Nature* 327:529; Potrykus, I. (1990) *Biotechnol* 8:535; Grimsley et al. (1987) *Nature* 325:177; Gould et al (1991) *Plant Physiol* 95:426; Ishida et al. (1996) *Nature Biotechnology* 14:745; and U.S. Pat. No. 5,591,616, and the references cited therein.

The Agrobacterium strain utilized in the methods of the invention is modified to contain a gene or genes of interest, or a nucleic acid to be expressed in the transformed cells. The nucleic acid to be transferred is incorporated into the T-region and is flanked by at least one T-DNA border sequence. A variety of Agrobacterium species are known in the art particularly for dicotyledon transformation. Such Agrobacterium can be used in the methods of the invention. See, for example, Hooykaas, P. J. (1989) *Plant Mol. Biol.* 13:327; Smith et al. (1995) *Crop Science* 35:301; Chilton, M. O. (1993) *Proc. Natl. Acad. Sci. USA* 90:3119; Mollony et al. N:*Monograph Theor Appl Genet* NY, Springer verlag 19:148, 1993; and Ishida et al. (1996) *Nature Biotechnol.* 14:745; Komari, T. et al. (1996) *The Plant Journal* 10:165; herein incorporated by reference.

In the Ti plasmid, the T-region is distinct from the vir region whose functions are responsible for transfer and integration. Binary vector systems have been developed where the manipulated disarmed T-DNA carrying foreign DNA and the vir functions are present on separate plasmids. In this manner, a modified T-DNA region comprising foreign DNA (the nucleic acid to be transferred) is constructed in a small plasmid which replicates in *E. coli*. This plasmid is transferred conjugatively in a tri-parental mating into *A. tumefaciens* which contains a compatible plasmid-carrying virulence gene. The vir functions are supplied in trans to transfer the T-DNA into the plant genome. Such binary vectors are useful in the practice of the present invention.

Preferred vectors of the invention are super-binary vectors. See, for example, U.S. Pat. No. 5,591,616 and EPA 0604662A1, herein incorporated by reference. Such a super-binary vector has been constructed containing a DNA region originating from the virulence region of Ti plasmid pTiBo542 (Jin et al. (1987) *J. Bacteriol* 169:4417–4425) contained in a super-virulent *Agrobacterium tumefaciens* A281 exhibiting extremely high transformation efficiency (Hood et al. (1984) *Biotechnol.* 2:702–709; Hood et al. (1986) *J. Bacteriol.* 168:1283–1290; Komari et al. (1986) *J. Bacteriol.* 166:88–94; Jin et al. (1987) *J. Bacteriol.* 169:4417–4425; Komari T. (1989) *Plant Science* 60:223–229; ATCC Accession No. 37394).

Super-binary vectors are known in the art and include pTOK162 (Japanese Patent Appl. (Kokai) No. 4-222527, EP-A-504,869, EP-A-604,662, and U.S. Pat. No. 5,591,616 herein incorporated by reference) and pTOK233 (Komari, T. (1990) *Plant Cell Reports* 9:303–306; and Ishida et al. (1996) *Nature Biotechnology* 14:745; herein incorporated by reference). Other super-binary vectors may be constructed by the methods set forth in the above references. Super-binary vector pTOK162 is capable of replication in both *E. coli* and in *A. tumefaciens*. Additionally, the vector contains the virB, virC, and virG genes from the virulence region of pTiBo542. The plasmid also contains an antibiotic resistance gene, a selectable marker gene, and the nucleic acid of interest to be transformed into the plant. The nucleic acid to be inserted into the sorghum genome is located between the two border sequences of the T region. Superbinary vectors of the invention can be constructed having the features described above for pTOK162.

The T-region of the super-binary vectors and other vectors for use in the invention are constructed to have restriction sites for the insertion of the genes to be delivered. Alternatively, the DNA to be transformed can be inserted in the T-DNA region of the vector by utilizing in vivo homologous recombination. See, Herrera-Esterella et al. (1983) *EMBO J.* 2:987–995; Horch et al. (1984) *Science* 223:496–498). Such homologous recombination relies on the fact that the super-binary vector has a region homologous with a region of pBR322 or other similar plasmid. Thus, when the two plasmids are brought together a desired gene is inserted into the super-binary vector by genetic recombination via the homologous regions.

As will be evident to one of skill in the art, now that a method has been provided for stable transformation of sorghum, any nucleic acid of interest can be used in the methods of the invention. For example, a sorghum plant can be engineered to express disease and insect resistance genes, genes conferring nutritional value, genes to confer male and/or female sterility, antifungal, antibacterial or antiviral genes, and the like. Likewise, the method can be used to transfer any nucleic acid to control gene expression. For example, the nucleic acid to be transferred could encode an antisense oligonucleotide.

Genes of interest are reflective of the commercial markets and interests of those involved in the development of the crop. Crops and markets of interest change and as developing nations open up world markets, new crops and technologies will emerge also. In addition, as our understanding of agronomic traits and characteristics such as yield and heterosis increase, the choice of genes for transformation will change accordingly. Crops of special interest include corn, soybeans, canola, sunflower, rapeseed, rice, tobacco, wheat, sorghum, and alfalfa. General categories of genes of interest include, for example, those genes involved in information, such as Zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics and commercial products.

Agronomically important traits such as oil, starch and protein content can be genetically altered in addition to using traditional breeding methods. Modifications include increasing content of oleic acid, saturated and unsaturated oils, increasing levels of lysine and sulfur and providing essential amino acids, and also modification of starch. Hordothionin protein modifications are described in European Patents WO96/38563, WO94/16078 and WO96/38562, the disclosures of which are incorporated herein in their entirety by reference. Another example is lysine and/or sulfur rich seed protein encoded by the soybean 2S albumin described in U.S. Ser. No. 08/618,911 filed Mar. 20, 1996, and the chymotrypsin inhibitor from barley (Williamson et al. *Eur. J. Biochem.* (1987) 165:99–106, the disclosures of each are incorporated by reference. Derivatives of the following genes can be made by site directed mutagenesis to increase the level of preselected amino acids in the encoded polypeptide. For example the gene encoding the barley high lysine polypeptide (BHL), is derived from barley chymotrypsin inhibitor, U.S. Ser. No. 08/740,682 filed Nov. 1, 1996, and PCT/US97/20441 filed Oct. 31, 1997, the disclosures of each are incorporated herein by reference. Other proteins include methionine-rich plant proteins such as from sunflower seed (Lilley, et al. *Proceedings of the World Congress on Vegetable Protein Utilization in Human Foods and Animal Feedstuffs*, Applewhite, H. (ed.); American Oil Chemists Soc., Champaign, Ill.; (1989) 497–502; corn (Pedersen, et al. *J. Biol. Chem.* (1986) 261:6279; Kirihara et al. *Gene* (1988) 71:359; and rice (Musumura, et al. *Plant Mol. Biol.* (1989) 12:123. These references are herein incorporated by reference. Other agronomically important genes encode latex, Floury 2, growth factors, seed storage factors and transcription factors.

Insect resistance genes may encode resistance to pests that have great yield drag such as rootworm or that European Corn Borer. For example, genes from the microorganism *Bacillus thuringiensis* encode toxic proteins that have been isolated, characterized and successfully used to lessen ECB infestation (U.S. Pat. No. 5,366,892, Foncerrada et al. *Gene Encoding a Coleopteran-active Toxin*). Other examples of genes useful in insect resistance include those encoding secondary metabolites and plant toxins.

Genes encoding disease resistance traits may include detoxification genes, such as against fumonosin or other toxins. Fumonisin-resistance can be used to transform plant cells normally susceptible to Fusarium or other toxin-producing fungus as described in U.S. Pat. No. 5,792,931. Other example are genes conferring viral resistance and antimicrobial peptides.

Herbicide resistance traits may include genes coding for resistance to herbicides which act to inhibit the action of acetolactate synthase (ALS), in particular, the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins, described in WO96/38563, WO94/16078 and WO96/38562; and U.S. Pat. No. 5,703,409 issued Dec. 30, 1997, provide descriptions of modifications of proteins for desired purposes.

Commercial traits can also be encoded on a gene or genes which could increase for example, starch for ethanol production, or provide expression of proteins. Another important commercial use of transformed plants is the production of polymers and bioplastics, such as described in U.S. Pat. No. 5,602,321, issued Feb. 11, 1997. Genes such as, B-ketothiolase, PHBase (polyhydroxyburyrate synthase) and acetoacetyl-CoA reductase (see Schubert et al. (1988) *J. Bacteriol.* 170) facilitate expression of polyhyroxyalkanoates (PHAs).

For convenience, the nucleic acid to be transferred can be contained within expression cassettes. The expression cassette will comprise a transcriptional initiation region linked to the nucleic acid or gene of interest. Such an expression cassette is provided with a plurality of restriction sites for insertion of the gene or genes of interest to be under the transcriptional regulation of the regulatory regions.

The transcriptional initiation region, the promoter, may be native or homologous or foreign or heterologous to the host, or could be the natural sequence or a synthetic sequence. By foreign is intended that the transcriptional initiation region is not found in the wild-type host into which the transcriptional initiation region is introduced. As used herein a chimeric gene comprises a coding sequence operably linked to transcription initiation region which is heterologous to the coding sequence.

The transcriptional cassette will include the in 5'–3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acid Res.* 15:9627–9639.

Alternatively, the gene(s) of interest can be provided on another expression cassette. Where appropriate, the gene(s) may be optimized for increased expression in the transformed plant. Where mammalian, yeast, or bacterial or dicot genes are used in the invention, they can be synthesized using monocot or sorghum preferred codons for improved expression. Methods are available in the art for synthesizing plant preferred genes. See, for example, U.S. Pat. Nos. 5,380,831, 5,436,391, and Murray et al. (1989) *Nucleic Acids Res.* 17:477–498, herein incorporated by reference.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) *PNAS USA*, 86:6126–6130); potyvirus leaders, for example, TEV leader (Tobacco Etch Virus) (Allison et al. (1986); MDMV leader (Maize Dwarf Mosaic Virus); *Virology*, 154:9–20), and human immunoglobulin heavy-chain binding protein (BiP), (Macejak, D. G., and P. Sarnow (1991) *Nature*, 353:90–94; untranslated leader from the coat protein mRNA of alfalfa mosaic virus (AMV RNA 4), (Jobling, S. A., and Gehrke, L., (1987) *Nature*, 325:622–625; tobacco mosaic virus leader (TMV), (Gallie, D. R. et al. (1989) *Molecular Biology of RNA*, pages 237–256; and maize chlorotic mottle virus leader (MCMV) (Lommel, S. A. et al. (1991) *Virology*, 81:382–385). See also, Della-Cioppa et al. (1987) *Plant Physiology*, 84:965–968. Other methods known to enhance translation can also be utilized, for example, introns, and the like.

The expression cassettes may contain one or more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells. Selectable marker genes are utilized for the selection of transformed cells or tissues. Selectable marker genes include genes encoding antibiotic resistance, such as those encoding neomycin phosphotransferase II (NEO) and hygromycin phosphotransferase (HPT) as well as genes conferring resist insensitive to the herbicide or for an enzyme that degrades or detoxifies the herbicide in the plant before it can act. (See DeBlock et al. (1987) *EMBO J*, 6:2513–2518; DeBlock et al. (1989) *Plant Physiol.*, 91:691–704; Fromm et al. (1990) 8:833–839. For example, resistance to glyphosate or sulfonylurea herbicides has been obtained by using genes coding for the mutant target enzymes, 5-enolpyruvylshikimate-3-phosphate synthase (EPSPS) and acetolactate synthase (ALS). Resistance to glufosinate ammonium, bromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to genes encoding: neomycin phosphotransferase II (Fraley et a. (1986) *CRC Critical Reviews in Plant Science*, 4:1–25); cyanamide hydratase (Maier-Greiner et al. (1991) *Proc. Natl. Acad. Sci. USA*, 88:4250–4264); aspartate kinase; dihydrodipicolinate synthase (Perl et al. (1993) *Bio/Technology*, 11:715–718); tryptophan decarboxylase (Goddijn et al. (1993) *Plant Mol. Bio.*, 22:907–912); dihydrodipicolinate synthase and desensitized aspartade kinase (Perl et al. (1993) *Bio/Technology*, 11:715–718); bar gene (Toki et al. (1992) *Plant Physiol.*, 100:1503–1507 and Meagher et al. (1996) and *Crop Sci*, 36:1367); tryptophane decarboxylase (Goddijn et al. (1993) *Plant Mol. Biol.*, 22:907–912); neomycin phosphotransferase (NEO) (Southern et al. (1982) *J. Mol. Appl. Gen.*, 1:327; hygromycin phosphotransferase (HPT or HYG) (Shimizu et al. (1986) *Mol. Cell Biol.*, 6:1074); dihydrofolate reductase (DHFR) (Kwok et al. (1986) *PNAS USA* 4552); phosphinothricin acetyltransferase (DeBlock et al. (1987) *EMBO J.*, 6:2513); 2,2-dichloropropionic acid dehalogenase (Buchanan-Wollatron et al. (1989) *J. Cell. Biochem.* 13D:330); acetohydroxyacid synthase (Anderson et al U.S. Pat. No. 4,761,373; Haughn et al. (1988) *Mol. Gen. Genet.* 221:266); 5-enolpyruvyl-shikimate-phosphate synthase (aroA) (Comai et al. (1985) *Nature* 317:741); haloarylnitrilase (Stalker et al., published PCT applon WO87/04181); acetyl-coenzyme A carboxylase (Parker et al. (1990) *Plant Physiol.* 92:1220); dihydropteroate synthase (sul I) (Guerineau et al. (1990) *Plant Mol. Biol.* 15:127); 32 kD photosystem II polypeptide (psbA) (Hirschberg et al. (1983) *Science*, 222:1346); etc.

Also included are genes encoding resistance to: chloramphenicol (Herrera-Estrella et al. (1983) *EMBO J.*, 2:987–992); methotrexate (Herrera-Estrella et al. (1983) *Nature*, 303:209–213; Meijer et al. (1991) *Plant Mol Bio.*, 16:807–820 (1991); hygromycin (Waldron et al. (1985) *Plant Mol. Biol.*, 5:103–108; Zhijian et al. (1995) *Plant Science*, 108:219–227 and Meijer et al. (1991) *Plant Mol. Bio.* 16:807–820); streptomycin (Jones et al. (1987) *Mol. Gen. Genet.*, 210:86–91); spectinomycin (Bretagne-Sagnard et al. (1996) *Transgenic Res.*, 5:131–137); bleomycin (Hille et al. (1986) *Plant Mol. Biol.*, 7:171–176); sulfonamide (Guerineau et al. (1990) *Plant Mol. Bio.*, 15:127–136); bromoxynil (Stalker et al. (1988) *Science*, 242:419–423); 2,4-D (Streber et al. (1989) *Bio/Technology*, 7:811–816); glyphosate (Shaw et al. (1986) *Science*, 233:478–481); phosphinothricin (DeBlock et al. (1987) *EMBO J.*, 6:2513–2518); spectinomycin (Bretagne-Sagnard and Chupeau (1996) *Transgenic Research* 5:131–137).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art.

See generally, G. T. Yarranton (1992) *Curr. Opin. Biotech.*, 3:506–511; Christopherson et al. (1992) *Proc. Natl. Acad. Sci. USA*, 89:6314–6318; Yao et al. (1992) *Cell*, 71:63–72; W. S. Reznikoff (1992) *Mol. Microbiol.*, 6:2419–2422; Barkley et al. (1980) *The Operon*, pp. 177–220; Hu et al. (1987) *Cell*, 48:555–566; Brown et al. (1987) *Cell*, 49:603–612; Figge et al. (1988) *Cell*, 52:713–722; Deuschle et al. (1989) *Proc. Natl. Acad. Aci. USA*, 86:5400–5404; Fuerst et al. (1989) *Proc. Natl. Acad. Sci. USA*, 86:2549–2553; Deuschle et al. (1990) *Science*, 248:480–483; M. Gossen (1993) PhD Thesis, University of Heidelberg; Reines et al. (1993) *Proc. Natl. Acad. Sci. USA*, 90:1917–1921; Labow et al. (1990) *Mol. Cell Bio.*, 10:3343–3356; Zambretti et al. (1992) *Proc. Natl. Acad. Sci. USA*, 89:3952–3956; Baim et al. (1991) *Proc. Natl. Acad. Sci. USA*, 88:5072–5076; Wyborski et al. (1991) *Nuc. Acids Res.*, 19:4647–4653; A. Hillenand-Wissman (1989) *Topics in Mol. and Struc. Biol.*, 10:143–162; Degenkolb et al. (1991) *Antimicrob. Agents Chemother.*, 35:1591–1595; Kleinschnidt et al. (1988) *Biochemistry*, 27:1094–1104; Gatz et al. (1992) *Plant J.*, 2:397–404; A. L. Bonin (1993) PhD Thesis, University of Heidelberg; Gossen et al. (1992) *Proc. Natl. Acad. Sci. USA*, 89:5547–5551; Oliva et al. (1992) *Antimicrob. Agents Chemother.*, 36:913–919; Hlavka et al. (1985) *Handbook of Exp. Pharmacology*, 78; Gill et al. (1988) Nature 334:721–724. Such disclosures are herein incorporated by reference.

The above list of selectable marker genes are not meant to be limiting. Any selectable marker gene can be used in the present invention.

Where appropriate, the selectable marker genes and other gene(s) and nucleic acid of interest to be transferred can be synthesized for optimal expression in sorghum. That is, the coding sequence of the genes can be modified to enhance expression in sorghum. The synthetic nucleic acid is designed to be expressed in the transformed tissues and plants at a higher level. The use of optimized selectable marker genes may result in higher transformation efficiency.

Methods for synthetic optimization of genes are available in the art. The nucleotide sequence can be optimized for expression in sorghum or alternatively can be modified for optimal expression in monocots. The plant preferred codons may be determined from the codons of highest frequency in the proteins expressed in sorghum. It is recognized that genes which have been optimized for expression in maize and other monocots can be used in the methods of the invention. See, for example, EPA 0359472; EPA 0385962; WO 91/16432; Perlak et al. (1991) *Proc. Natl. Acad. Sci. USA*, 88:3324–3328; and Murray et al. (1989) *Nucleic Acids Research*, 17: 477–498. U.S. Pat. No. 5,380,831; U.S. Pat. No. 5,436,391; and the like, herein incorporated by reference. It is further recognized that all or any part of the gene sequence may be optimized or synthetic. That is, fully optimized or partially optimized sequences may also be used.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The methods of the invention are useful for transforming sorghum plant cells. Such cells include callus which can be originated from any tissues of sorghum plants. Preferably, the tissue utilized in initiating callus is immature tissue such as immature embryos, immature inflorescences, and the basal portion of young leaves. Alternatively, the callus can be originated from anthers, microspores, mature embryos, and in principal from any other tissue of sorghum capable of forming callus and/or secondary embryos. A useful tissue for producing regenerable callus is the scutellum of immature sorghum embryos. Of particular interest, are the use of immature embryos. Such embryos can be isolated from immature kernels and treated for transformation. Alternatively, the embryos can be isolated and cultured for several days, generally about 3 to about 10 days, preferably about 5 to about 8 days, prior to inoculation with Agrobacterium.

The method can also be used to transform cell suspensions. Such cell suspensions can be formed from any sorghum tissue.

Immature embryos are an intact tissue that is capable of cell division to give rise to callus cells that can then differentiate to produce tissues and organs of the whole plant. Immature embryos can be obtained from the fertilized reproductive organs of a mature sorghum plant. Exemplary methods for isolating immature embryos are described by Green and Phillips (1976) *Proc. Sci.* 15:417–421. See also Neuffer et al. in Maize for Biological Research W. F. Sheridan (EP) University Press, University of North Dakota, Grand Forks, N.Dak., 1982, herein incorporated by reference. Immature embryos are preferably aseptically isolated from the developing kernel and held in sterile medium until use. The immature embryos are preferably used at approximately two (2) days to about 20 days after pollination, more preferably about 4 days to about 16 days after pollination, and still more preferably about 5 days to about 12 days after pollination. Generally, the embryos exposed to Agrobacterium range from about 0.3 to about 4 mm in size, more preferably about 0.6 to about 3.0 mm, still more preferably about 0.8 to about 1.5 mm.

The Agrobacterium-mediated transformation process of the invention can be broken into several steps. The basic steps include an infection step (step 1); a co-cultivation step (step 2); an optional resting step (step 3); a selection step (step 4); and a regeneration step (step 5).

An optional preculture step may be added prior to the infection step. The preculture step involves culturing the immature embryos or other target tissue prior to the infection step on a suitable medium such as N6, LSD1.5, or PHI-J medium. (See Example 2). The preculture period may vary from about 1 to about 10 days, preferably about 3 to about 7 days, more preferably about 5 to about 6 days. Such a preculture step was found to prevent transformation of maize cultures. See EP0672752A1.

In the infection step, the cells to be transformed are isolated and exposed to Agrobacterium. If the target cells are immature embryos, the embryos are isolated and the cells contacted with a suspension of Agrobacterium. As noted above, the Agrobacterium has been modified to contain a gene or nucleic acid of interest. The nucleic acid is inserted into the T-DNA region of the vector. General molecular techniques used in the invention are provided, for example, by Sambrook et al. (eds.) *Molecular Cloning: A Laboratory Manual*, 1989, Cold Spring Harbor Laboratory Press, Cold Spring Harbor, N.Y.

Agrobacterium containing the plasmid of interest are preferably maintained on Agrobacterium master plates with stock frozen at about −80° C. As used herein, the term "Agrobacterium capable of transferring at least one gene" refers to Agrobacterium containing the gene or nucleic acid of interest, generally in a plasmid that is suitable for mediating the events required to transfer the gene to the cells to be infected. Master plates can be used to inoculate agar plates to obtain Agrobacterium which is then resuspended in media for use in the infection process. Alternatively, bacteria from the master plate can be used to inoculate broth cultures that are grown to logarithmic phase prior to transformation.

The concentration of Agrobacterium used in the infection step and co-cultivation step can affect the transformation frequency. Likewise, very high concentrations of Agrobacterium may damage the tissue to be transformed, such as the immature embryos, and result in a reduced callus response. Thus, the concentration of Agrobacterium useful in the methods of the invention may vary depending on the Agrobacterium strain utilized, the tissue being transformed, the sorghum genotype being transformed, and the like. To optimize the transformation protocol for a particular sorghum line or tissue, the tissue to be transformed, (immature embryos, for example), can be incubated with various concentrations of Agrobacterium. Likewise, the level of marker gene expression and the transformation efficiency can be assessed for various Agrobacterium concentrations. While the concentration of Agrobacterium may vary, generally a concentration range of about $1 \times 10^3$ cfu/ml to about $1 \times 10^{10}$ preferably within the range of about $1 \times 10^3$ cfu/ml to about $1.5 \times 10^9$ cfu/ml and still more preferably at about $0.5 \times 10^9$ cfu/ml to about $1.0 \times 10^9$ cfu/ml will be utilized.

The tissue to be transformed is generally added to the Agrobacterium suspension in a liquid contact phase containing a concentration of Agrobacterium to optimize transformation efficiencies. The contact phase facilitates maximum contact of the cells/tissue to be transformed with the suspension of Agrobacterium. The cells are contacted with the suspension of Agrobacterium for a period of at least about three (3) minutes to about 15 minutes, preferably about 4 minutes to about 10 minutes, more preferably about 5 minutes to about 8 minutes.

The liquid contact phase of the infection step takes place in a liquid solution that includes the major inorganic salts and vitamins of N6 medium referred to herein as "N6 salts" (Chu C. C. Proc. Symp. Plant Tissue Culture, Science Press Peking. pp. 43–50, 1987). As used herein, medium containing "N6 salts" includes medium containing about 400–500 mg/l ammonium sulfate and preferably about 463.0 mg/l ammonium sulfate; about 1.0–2.0 mg/l boric acid and preferably about 1.6 mg/l boric acid; about 100–140 mg/l calcium chloride anhydrous and preferably about 125 mg/l calcium chloride anhydrous; about 20–50 mg/l Na2-EDTA and preferably about 37.25 mg/l $Na_2$-EDTA; about 20–40 mg/l ferrous sulfate.$7H_2O$ and preferably about 27.8 mg/l ferrous sulfate.$7H_2O$; about 80–100 mg/l magnesium sulfate and preferably about 90.37 mg/l magnesium sulfate; about 1.5–7 mg/l magnesium sulfate.$H_2O$ and preferably about 3.33 mg/l manganese sulfate.$H_2O$; about 0.4–1.6 mg/l potassium iodide and preferably about 0.8 mg/l potassium iodide; about 1,500–3,500 mg/l potassium nitrate and preferably about 2,830 mg/l potassium nitrate; about 200–600 mg/l potassium phosphate monobasic and preferably about 400 mg/l potassium phosphate monobasic; and, about 1.0–2.5 mg/l zinc sulfate.$7H_2O$ and preferably about 1.5 mg/l zinc sulfate.$7H_2O$.

Other equivalent liquid suspensions are known in the art and can be used. See, for example, Ishida et al. (1996) Nature Biotechnology 14:745–750; EPA 0672752A1; EPA 0687730A1; and U.S. Pat. No. 5,591,616. For example, media containing MS salts can also be used in the infection step. MS salts include about 1,650.0 mg/l ammonium nitrate, about 6.2 mg/l boric acid, about 332.2 mg/l calcium chloride anhydrous, about 0.025 mg/l cobalt chloride.$6H_2O$, about 0.025 mg/l cupric sulfate.$5H_2O$, about 37.26 mg/l $Na_2$-EDTA, about 27.8 mg/l ferrous sulfate.$7H_2O$, about 180.7 mg/l magnesium sulfate, about 16.9 mg/l manganese sulfate.$H_2O$, about 0.25 mg/l molybdic acid (Sodium salt).$2H_2O$, about 0.83 mg/l potassium iodide, about 1,900.0 mg/l potassium nitrate, about 170.0 mg/l potassium phosphate monobasic, and about 8.6 mg/l zinc sulfate.$7H_2O$. Additionally, other media, such as LS and those set forth in the examples, can be utilized. The macro and micro salts in MS medium are identical to the macro and micro salts in LS medium, but the two media differ in the composition of some of the vitamins and other components (Skirvin R. M., In: Cloning Agricultural Plants Via In Vitro Techniques, B. V. Conger, ed., CRC Press, Knoxville, Tenn., pp. 51–140, 1981).

In addition, the media in the infection step generally excludes $AgNO_3$. $AgNO_3$ is generally included in the co-cultivation, resting (when used) and selection steps when N6 media is used.

In the co-cultivation step, the cells to be transferred are co-cultivated with Agrobacterium. For immature embryos, the co-cultivation with the Agrobacterium takes place on a solid medium. The embryos are positioned axis down on the solid medium and the medium can include $AgNO_3$ at a range of about 0.85 to 8.5 mg/l, although 0.01 to 200 mg/l can also be used. The embryos are co-cultivated with the Agrobacterium for about 1–30 days, preferably about 2–20 days and more preferably about 3–10 days.

Following the co-cultivation step, the transformed cells may be subjected to a resting step. As noted above, the resting step is optional. Where no resting step is used, an extended co-cultivation step may utilized to provide a period of culture time prior to the addition of a selective agent.

For the resting step, the transformed cells are transferred to a second medium containing an antibiotic capable of inhibiting the growth of Agrobacterium. This resting phase is performed in the absence of any selective pressures to permit preferential initiation and growth of callus from the transformed cells containing the heterologous nucleic acid. An antibiotic is added to inhibit Agrobacterium growth. Such antibiotics are known in the art which inhibit Agrobacterium and include Cefotaxime, timetin, vancomycin, carbenicillin, and the like. Concentrations of the antibiotic will vary according to what is standard for each antibiotic. For example, concentrations of carbenicillin will range from about 50 mg/l to about 250 mg/l carbenicillin in solid media, preferably about 75 mg/l to about 200 mg/l, more preferably about 100–125 mg/l. Those of ordinary skill in the art of monocot sulfate.7H2O transformation will recognize that the concentration of antibiotic can be optimized for a particular transformation protocol without undue experimentation.

The resting phase cultures are preferably allowed to rest in the dark at 28° C. for about 1 to about 15 days, preferably for about 3 to about 10 days, more preferably for about 5 to about 8 days. Any of the media known in the art can be utilized for the resting step.

Following the co-cultivation step, or following the resting step, where it is used, the transformed cells are exposed to selective pressure to select for those cells that have received and are expressing polypeptide from the heterologous nucleic acid introduced by Agrobacterium. Where the cells are embryos, the embryos are transferred to plates with solid medium that includes both an antibiotic to inhibit growth of the Agrobacterium and a selection agent. The agent used to select for transformants will select for preferential growth of explants containing at least one selectable marker insert positioned within the superbinary vector and delivered by the Agrobacterium.

Generally, any of the media known in the art suitable for the culture of sorghum can be used in the selection step, such as media containing N6 salts or MS salts. During selection, the embryos are cultured until callus formation is observed. Typically, calli grown on selection medium are allowed to grow to a size of about 1.5 to about 2 cm. diameter.

After the calli have reached the appropriate size, the calli are cultured on regeneration medium in the dark for several weeks, generally about 1 to 3 weeks to allow the somatic embryos to mature. Preferred regeneration media include media containing MS salts, such as PHI-E and PHI-F media as provided in the Examples. The calli are then cultured on rooting medium in a light/dark cycle until shoots and roots develop. Methods for plant regeneration are known in the art and preferred methods are provided by Kamo et al. (*Bot. Gaz* 146(3):327–334, 1985), West et al. (*The Plant Cell* 5:1361–1369, 1993), and Duncan et al. (*Planta* 165:322–332, 1985).

Small plantlets are then transferred to tubes containing rooting medium and allowed to grow and develop more roots for approximately another week. The plants are then transplanted to soil mixture in pots in the greenhouse.

Now that it has been demonstrated that sorghum can be transformed utilizing Agrobacterium, alterations to the general method described herein can be used to increase efficiency or to transform elite inbred lines which may exhibit some recalcitrance to transformation. Factors that affect the efficiency of transformation include the types and stages of tissues infected, the concentration of *A. tumefaciens*, composition of the media for tissue culture, selectable marker genes, the length of any of the above-described steps involved, kinds of vectors and Agrobacterium strains, and the sorghum genotype. Therefore, these and other factors may be varied to determine what is an optimal transformation protocol for any particular sorghum line. It is recognized that not every genotype will react the same to the transformation conditions and may require a slightly different modification of the protocol. However, by altering each of the variables, an optimum protocol can be derived for any sorghum line.

While any sorghum line or variety can be used in the transformation methods of the invention, examples of sorghum lines include but are not limited to public lines such as CS3541, M91051, SRN39, Shanqui red, IS8260, IS4225, Tx430, P898012, P954035, PP290 (Casas et al. supra) and commercially important Pioneer proprietary inbred lines such as PH860, PH987, PHB180, PHB123, and PHB82.

Further modifications may be utilized including providing a second infection step to increase infection by the Agrobacterium. Also, the vectors and methods of the invention can be used in combination with particle bombardment to produce transformed sorghum plants. Particle bombardment can be used to increase wounding in the tissues to be transformed by Agrobacterium. (Bidney et al. (1990) *Plant Mol. Biol.* 18:301–313; EP0486233, herein incorporated by reference). Methods for particle bombardment are well known in the art. See, for example, Sanford et al., U.S. Pat. No. 4,945,050; McCabe et al. (1988) *Biotechnology*, 6:923–926). Also see, Weissinger et al. (1988) *Annual Rev. Genet.*, 22:421–477; Datta et al. (1990) *Biotechnology*, 8:736–740; Klein et al. (1988) *Proc. Natl. Acad. Sci. USA*, 85:4305–4309; Klein et al. (1988) *Biotechnology*, 6:559–563 (maize); Klein et al. (1988) *Plant Physiol.*, 91:440–444; Fromm et al. (1990) *Biotechnology*, 8:833–839; and Tomes et al. "Direct DNA transfer into intact plant cells via microprojectile bombardment." In: Gamborg and Phillips (Eds.) Plant Cell, Tissue and Organ Culture: Fundamental Methods; Springer-Verlag, Berlin (1995); Hooydaas-Van Slogteren & Hooykaas (1984) *Nature* (London), 311:763–764; Bytebier et al. (1987) *Proc. Natl. Acad. Sci. USA*, 84:5345–5349; all of which are herein incorporated by reference.

After wounding of the cells by microprojectile bombardment, the cells are inoculated with Agrobacterium solution. The additional infection step and particle bombardment may be useful in transforming those genotypes of sorghum which are particularly recalcitrant to infection by Agrobacterium.

The following examples are offered by way of illustration and not by way of limitation.

EXPERIMENTAL

Example 1

Construction of Agrobacterium Vectors and Strains

Figure 1:
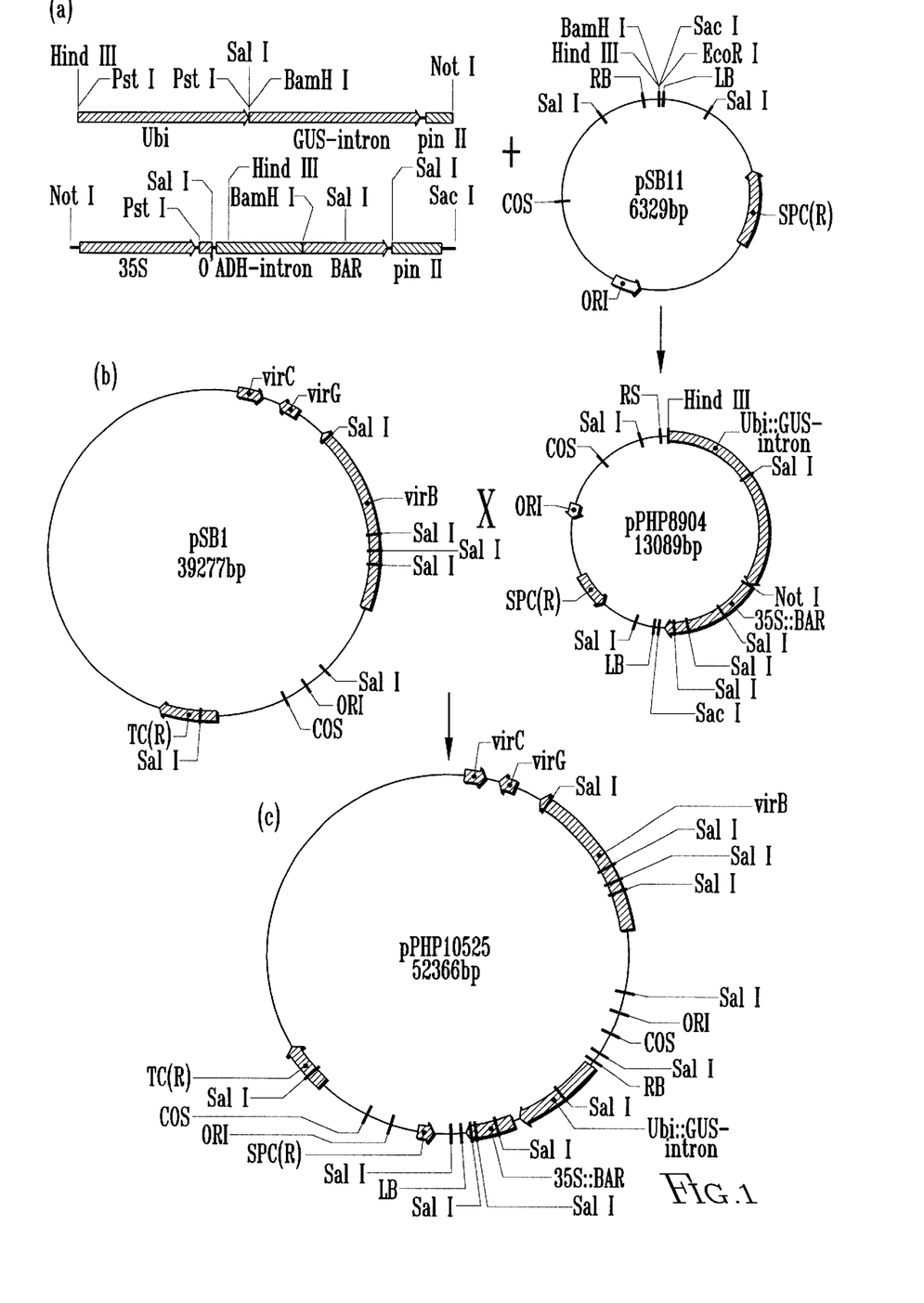
FIG. 1 provides a diagram illustrating the construction of vector pPHP10525.

PHP10525:

All vectors were constructed using standard molecular biology techniques (Sambrook et al. (eds.), supra). A reporter gene and a selectable marker gene for gene expression and selection was inserted between the T-DNA borders of a superbinary vector. The reporter gene included the β-glucuronidase (GUS) gene (Jefferson, R. A. et al (1986) *Proc. Natl. Acad. Sci (USA)* 83:8447–8451) into whose coding region was inserted the second intron from the potato ST-LS1 gene (Vancanneyt et al. (1990) *Mol. Gen. Genet.* 220:245–250), to produce intron-GUS, in order to prevent expression of the gene in Agrobacterium (see Ohta, S. et al. (1990) *Plant Cell Physiol.* 31(6):805–813). Referring to FIG. 1(*a*), the 2 kb fragment of the promoter region of the maize ubiquitin gene Ubi-1 (Christensen et al. (1992) *Plant Mol. Biol.* 18:675–689), with added 5' BamHI site of the GUS gene. A fragment containing bases 2 to 310 from the terminator of the potato proteinase inhibitor (pinII) gene (An et al. (1989) *Plant Cell* 1:115–122) was blunt-end ligated downstream of the GUS coding sequence, to create the GUS expression cassette. The 3' end of the terminator carried a NotI restriction site.

For the selectable marker, a Cauliflower Mosaic Virus 35S promoter with a duplicated enhancer region (2×35S; bases −421 to −90 and −421 to +2 from Gardner et al. (1981) *Nucl. Acids Res.* 9:2871–2888) with a flanking 5' NotI site and a 3' PstI site was created. A PstI/SalI fragment containing the 79 bp Tobacco Mosaic Virus leader (Gallie et al. (1987) *Nucl. Acids Res.* 15:3257–3273) was inserted downstream of the promoter followed by a SalI/BamHI fragment containing the first intron of the maize alcohol dehydrogenase gene ADH1-S (Dennis et al. (1984) *Nucl. Acids Res.* 12:3983–3990). The BAR coding sequence (Thompson et al. (1987) *EMBO J.* 6:2519–2523) was cloned into the BamHI site, with the pinII terminator ligated downstream, to create the BAR expression cassette. The pinII terminator was flanked by a 3' SalI site.

The plasmid, pPHP8904 (FIG. 1*b*) was constructed by inserting the GUS expression cassette as a HindIII/NotI fragment and the BAR expression cassette as a NotI/SacI fragment between the right and left T-DNA borders in pSB11 and HindIII and SacI sites. The GUS cassette was inserted proximal to the right T-DNA border. The plasmid pSB11 was obtained from Japan Tobacco Inc. (Tokyo, Japan). The construction of pSB11 from pSB21 and the construction of pSB21 from starting vectors is described by Komari et al. (1996) *Plant J.* 10:165–174. The T-DNA of pPHP8904 was integrated into the superbinary plasmid pSB1 (Saito et al., EP 672 752 A1) by homologous recombination between the two plasmids (FIG. 1, pSB1× pPHP8904). The plasmid pSB1 was also obtained from Japan Tobacco Inc. *E. coli* strain HB101 containing pPHP8904 was mated with Agrobacterium strain LBA4404 harboring pSB1 to create the cointegrate plasmid in Agrobacterium, designated as LBA4404 (pPHP10525) as shown in FIG. 1c, using the method of Ditta et al. (1980) *Proc. Natl. Acad. Sci. USA* 77:7347–7351. LBA4404 (pPHP10525) was selected based on resistance of transformed Agrobacterium to spectinomycin and verified as a recombinant by a SalI restriction digest of the plasmid.

PHP11264:

PHP11264 was basically constructed as described above. One difference noted is the selectable marker gene. For the selectable marker, a maize ubiquitin (UBI) promoter (Christensen et al. (1992) *Plant Mol. Biol.* 18:675–689), with added 5' of the BAR gene. The UBI intron was inserted downstream of the promoter. The BAR coding sequence was cloned downstream of the UBI intron (Thompson et al. (1984) *Nuc. Acids Res.* 12:3983–3990). A fragment containing bases 2 to 310 from the terminator of the potato proteinase inhibitor (pinII) gene (An et al. (1989) *Plant Cell* 1:115–122) was ligated downstream of the BAR coding sequence, to create the BAR expression cassette. See FIG. 2.

Example 2

Transformation of a Drought-resistant Sorghum Cultivar P898012

Preparation of Agrobacterium Suspension:

Single colonies were selected from matings and streaked out sequentially at least three times to ensure purity of the Agrobacterium strain. From the final streaked plates, a single colony was selected and used to initiate a liquid culture. Following growth to stationary phase, the liquid culture was used to make glycerol stocks and miniprep plasmid DNA. Sambrook et al., supra. The resulting plasmid DNA was digested with SalI to verify the co-integrate LBA4404(pPHP10525). The glycerol stocks were stored at −80° C. and were used as the source for master plates.

Agrobacterium was streaked out from a −80° frozen aliquot onto a plate containing PHI-L medium and cultured at 28° C. in the dark for 3 days. PHI-L media comprised 25 ml/l Stock Solution A, 25 ml/l Stock Solution B, 450.0 ml/l Stock Solution C and spectinomycin (Sigma Chemicals) added to a concentration of 50 mg/l in sterile ddH$_2$O (stock solution A: K$_2$HPO$_4$ 60.0 g/l, NaH$_2$PO$_4$ 20.0 g/l, adjust pH to 7.0 w/KOH and autoclave; stock solution B: NH$_4$Cl 20.0 g/l, MgSO$_4$.7H$_2$O 6.0 g/l, KCl 3.0 g/l, CaCl$_2$ 0.20 g/l, FeSO$_4$.7H$_2$O 50.0 mg/l, autoclave; stock solution C: glucose 5.56 g/l, agar 16.67 g/l (*A-7049, Sigma Chemicals, St. Louis, Mo.) and autoclave).

The plate can be stored at 4° C. and used usually for about 1 month. Several colonies were picked from the master plate and streaked onto plate containing PHI-M medium [yeast extract (Difco) 5.0 g/l/peptone (Difco) 10.0 g/l; Nacl 5.0 g/l; agar (Difco) 15.0 g/l; pH 6.8, containing 50 mg/L spectinomycin] and incubated at 28° C. in the dark for 2 days.

Five ml of either PHI-G [100 ml/l of a 10×solution of N6 macronutrients (463.0 mg/l (NH$_4$)$_2$SO$_4$, 400.0 mg/l KH$_2$PO$_4$, 125.33 mg/l CaCl$_2$, 90.37 mg/l MgSO$_4$ and 2,830.0 mg/l KNO$_3$), 2.44 mg/l Boric acid, 37.1 mg/l Na$_2$-EDTA.2H$_2$O, 27.88 mg/l FeSO4.7H$_2$O, 7.33 mg/l MnSO$_4$.H$_2$O, 0.77 mg/l KI, 0.6 mg/l ZnSO$_4$.7H$_2$O, 0.15 mg/l Na$_2$MoO2.2H$_2$O, 1.68 g/l KNO$_3$, 0.8 mg/l glycine, 3.2 mg/l nicotinic acid, 3.2 mg/l Pyridoxine.HCl, 3.4 mg/l Thiamine.HCl, 0.6 g/l Myo-inositol, 0.8 mg/l 2,4-D, 1.2 mg/l Dicamba (Sigma), 1.98 g/l L-proline, 0.3 g/l casein hydrolysate, 68.5 g/l sucrose and 36.0 g/l glucose, pH 5.2] or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1.0 g/l; 2, 4-D 1.5 mg/l; sucrose 68.50 g/l; glucose 36.0 g/l; adjust pH to 5.2 w/KOH and filter-sterilize] and 5 µl of 100 mM (3'-5'-Dimethoxy-4'-hydroxyacetophenone, Aldrich chemicals) were added to a 14 ml Falcon tube in a hood. About 3 full loops (5 mm loop size) Agrobacterium was collected from a plate and suspended in the tube, then the tube was vortexed to make an even suspension. One ml of the suspension was transferred to a spectrophotometer tube and the OD of the suspension was adjusted to 0.72 at 550 nm by adding either more Agrobacterium or more of the same suspension medium. The Agrobacterium concentration was approximately 1×10$^9$ cfu/ml. The final Agrobacterium suspension was aliquoted into 2 ml microcentrifuge tubes, each containing 1 ml of the suspension. The suspensions were then used as soon as possible.

Embryo Isolation, Infection and Co-cultivation:

Sorghum immature embryos of about 0.8 to about 1.5 mm were isolated from sterilized immature kernels of sorghum line P898012, a drought-resistant sorghum cultivar obtained from Purdue University. The immature kernels were removed from a sorghum head and placed in an autoclaved glass jar. These immature kernels were immersed in 50% bleach and 0.1% Tween 20 in this jar and the jar was shaken well to allow the solution to cover all kernels and to reach everywhere inside the jar. Apply vacuum for 10 minutes and rinse with autoclaved deionized distilled water, twice in a hood and these kernels were kept in sterile water until use. The immature embryos were isolated from sterilized kernels using a sterile spatula (Baxter Scientific Products S1565). The isolated embryos were cultured on PHI-J medium without acetosyringone in the dark at about 25° C. for 5 days and these precultured embryos were inoculated with 10$^9$ cfu/ml Agrobacterium suspension. The Agrobacterium was suspended in PHI-G medium. About 1 ml of Agrobacterium suspension was added to about 100 isolated embryos in a sterile tube and the tube vortexed for 30 sec. The tube was allowed to stand for 5 min. in the hood. The suspension of Agrobacterium and embryos was poured into a Petri plate containing PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2, 4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 µM acetosyringone with a final pH of 5.8. PHI-B medium can also be used. PHI-B medium: [CHU(N6) basal salts (Sigma C-1416) 4.0 g/l; Eriksson's vitamin mix (1000×, Sigma-1511) 1.0 ml/l; thiamine.HCl 0.5 mg/l; 2.4-D 1.5 mg/l; L-proline 0.69 g/l; silver nitrate 0.85 mg/l; gelrite (Sigma) 3.0 g/l; sucrose 30.0 g/l; acetosyringone 100 µM; pH 5.8].

Any embryos left in the tube were transferred to the plate using a sterile spatula. The Agrobacterium suspension was drawn off and the embryos placed axis side down on the media. The plate was sealed with Parafilm tape or Pylon Vegetative Combine Tape Product named "E.G.CUT" and is available in 18 mm×50 m sections; Kyowa Ltd., Japan), and incubated in the dark at about 25° C. for an additional 5 days of co-cultivation.

Resting Step:

No resting step was utilized.

Selection and Regeneration Steps:

For selection, all of the embryos were then transferred to new plates containing PHI-J medium without glucose and acetosyringone, but adding 100 mg/l carbenicillin and 5 mg/l phosphinothricin (PPT), as a selection medium, putting about 20 embryos onto each plate. The plates were sealed as described above and incubated in the dark at 25° C. for the first two weeks of selection. The embryos were then transferred to fresh selection medium at the end of two weeks. After a period of another 2 week culture, these embryos were sub-cultured onto the same PHI-J medium except PPT was increased from 5 mg/l to 10 mg/l. The embryos were then transferred to fresh selection medium containing 10 mg/l PPT at 3 week intervals continuing at 25° C. in the dark. The tissue was subcultured by transferring to fresh selection medium for a total of about 3.5 months to obtain herbicide-resistant calli.

For regeneration, the callus was then cultured on PHI-E medium [MS salts 4.3 g/l; myo-inositol 0.1 g/l; nicotinic acid 0.5 mg/l; thiamine.HCl 0.1 mg/l; Pyridoxine.HCl 0.5 mg/l; Glycine 2.0 mg/l; Zeatin 0.5 mg/l; sucrose 60.0 g/l; Agar (Sigma, A-7049) 8.0 g/l; Indoleacetic acid (IAA, Sigma) 1.0 mg/l; Abscisic acid (ABA, Sigma) 0.1 $\mu$M; PPT 10 mg/l; carbenicillin 100 mg/l adjusted to pH 5.6] in the dark at 28° C. for 1–3 weeks to allow somatic embryos to mature. The callus was then cultured on PHI-F medium [MS salts 4.3 g/l; myo-inositol 0.1 g/l; Thiamine.HCl 01. mg/l; Pyridoxine.HCl 0.5 mg/l; Glycine 2.0 mg/l; nicotinic acid 0.5 mg/l; sucrose 40.0 g/l; gelrite 1.5 g/l; pH 5.6] at 25° C. under a daylight schedule of 16 hrs. light (270 uE m$^{-2}$sec$^{-1}$) and 8 hrs. dark until shoots and roots developed. Each small plantlet was then transferred to a 25×150 mm tube containing PHI-F medium and grown under the same conditions for approximately another week. The plants were transplanted to pots with soil mixture in a greenhouse. GUS+events were determined at the callus stage or regenerated plant stage.

Confirmation of Stable Transformation:

25 T0 plants have been regenerated from the callus and grown in the greenhouse. Five plants were chosen at random for PCR assay for the presence of BAR and Gus genes. The PCR result confirmed that all of the 5 plants were stably transformed with Agrobacterium.

The 25 plants, as well as non-transformed control plants, were painted with a 1% solution of the herbicide Liberty on their leaves to verify herbicide resistance due to the expression of the BAR gene. All of the 25 regenerated plants were Liberty resistant while the control plants exhibited sensitivity to Liberty.

Example 3

Optimizing the Transformation Procedure for Particular Sorghum Lines

Using the methods detailed above in Examples 1 and 2, transformation protocols can be optimized for any sorghum genotype. To demonstrate, the following protocol sets forth particular parameters that can be tested for an effect on transformation efficiency. It is recognized that other protocols can be formulated and other sorghum lines tested. The following is an illustration of steps to optimize transformation.

Figure 2:
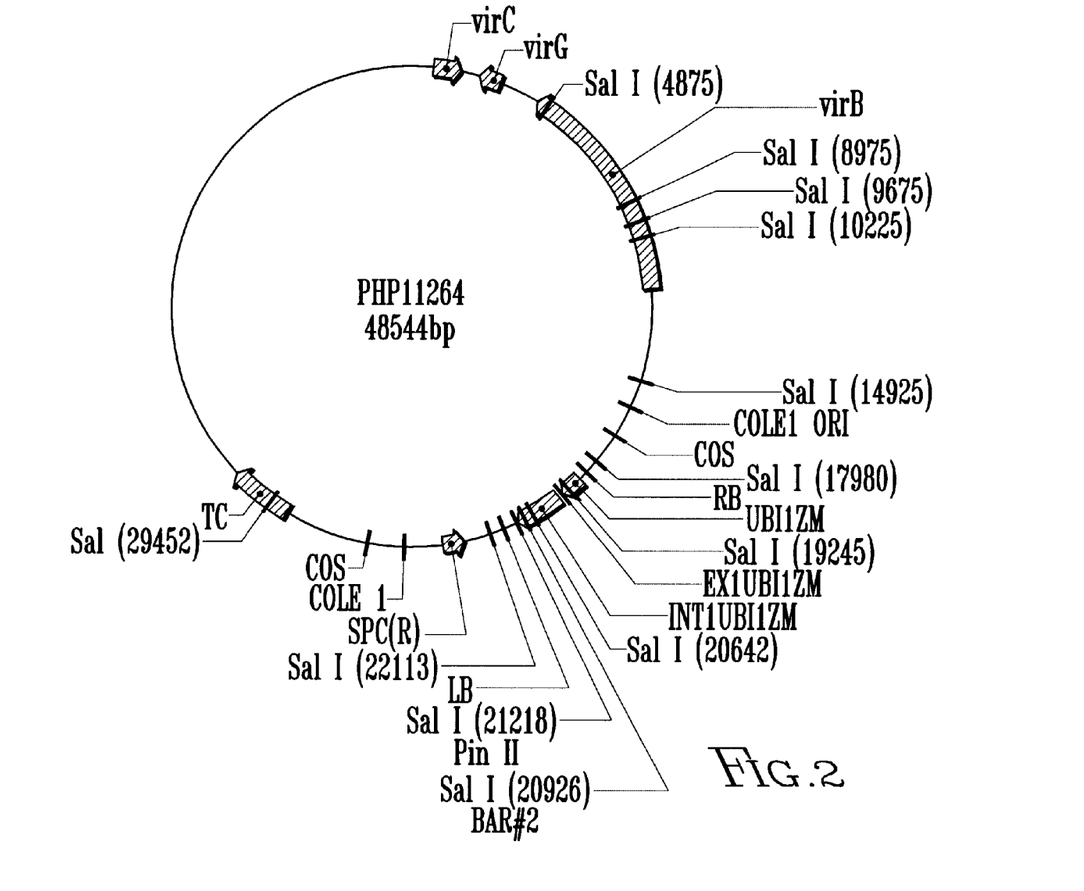
FIG. 2 provides a plasmid map of vector pPHP11264.

Materials:

Agrobacterium Stain: LBA4404 (PHP11264) (UBI-UBI intron-Bar-PinII) (FIG. 2).

Sorghum Lines: P898012 and PH391 (a Pioneer elite inbred).

Treatments:

The following table illustrates a number of treatments that will indicate which factors are important for efficient transformation of the two exemplary sorghum lines.

TABLE 1

Treatment Conditions

| Treat-ment | P898012 Conditions | Embryos | PH391 Conditions | Embryos |
|---|---|---|---|---|
| 1 | Fresh embryo with Agroinfection, co-cultivation for 3 days & resting for 4 days | 50–100 | Fresh embryo with Agroinfection, co-cultivation for 3 days & resting for 4 days | 50–100 |
| 2 | Fresh embryo with Agroinfection, co-cultivation for 7 days and no resting | 50–100 | Fresh embryo with Agroinfection, co-cultivation for 7 days and no resting | 50–100 |
| 3 | Fresh embryo 1$^{st}$ infection and 2$^{nd}$ infection at the 3$^{rd}$ day of co-cultivation, additional 4 days for 2$^{nd}$ co-cultivation and no resting | 50–100 | Fresh embryo 1$^{st}$ infection and 2$^{nd}$ infection at the 3$^{rd}$ day of co-cultivation, additional 4 days for 2$^{nd}$ co-cultivation and no resting | 50–100 |
| 4 | Pre-culture 7 days and then Agroinfection, co-cultivation for 7 days and no resting | 50–100 | Pre-culture 7 days and Agroinfection, co-cultivation for 7 days and no resting | 50–100 |
| 5 | Pre-culture 7 days, bombarding and Agroinfection, co-cultivation for 7 days and no resting | 50–100 | Pre-culture 7 days, bombarding and Agroinfection, co-cultivation for 7 days and no resting | 50–100 |
| 6 | no Agroinfection control | 20 | no Agroinfection control | 20 |

Detailed Procedure of these Experiments

A brief description of the treatments set forth in Table 1 is provided below. Generally, the treatment protocols will be performed for each of the sorghum lines and will follow the details given in Examples 1 and 2 with the following differences.

Treatment-1: Fresh sorghum immature embryos of 0.8 to 1.5 mm are isolated from sterilized immature kernels. The isolated embryos are inoculated with 10$^9$ cfu/ml Agrobacterium suspension (Agrobacterium suspended in PHI-I medium) and co-cultivated with Agrobacterium on PHI-J medium plus 10 mg/l ascorbic acid at 25° C. in the dark for about 3 days. After co-cultivation, the embryos are transferred to PHI-J medium plus 10 mg/l ascorbic acid ascorbic acid without glucose and acetosyringone for about 4 days for a resting step. After the resting step, all of the embryos are then transferred to new plates containing PHI-J medium plus 10 mg/l ascorbic acid without glucose and acetosyringone, but adding 100 mg/l carbenicillin and 5 mg/l PPT or 1.5 mg/l Bialaphos as a selection medium. After a culture period of 2 weeks, the embryos will be subcultured onto the same PHI-J medium except that PPT is increased from 5 mg/l to 10 mg/l or Bialaphos is increased from 1.5 mg/l to 3 mg/l. The selection procedure will be similar to that used in Example 2 except that either PPT or Bialaphos can be used as the selective agents. After the well-growing callus is recovered, the callus is moved to PHI-E. The calli are then cultured on PHI-F medium under a daylight schedule of 16 hrs. light (270 uE m$^{-2}$sec$^{-1}$) and 8 hrs. dark until shoots and roots develop. Each small plantlet is then transferred to a 25×150 mm tube containing PHI-F medium and grown under the same conditions for approximately another week. The plants are transplanted to pots with soil mixture in a greenhouse. Stable transformation will be confirmed by DNA analysis and herbicide resistance.

Treatment-2: Fresh sorghum immature embryos of 0.8 to 1.5 mm are isolated from sterilized immature kernels. The isolated embryos are inoculated with 10$^9$ cfu/ml Agrobacterium suspension (Agrobacterium suspended in PHI-I medium) and co-cultivated with Agrobacterium on PHI-J medium plus 10 mg/l ascorbic acid at 25° C. in the dark for about 7 days. No resting step will be applied. After co-cultivation, all of the embryos are then transferred to new plates containing PHI-J medium plus 10 mg/l ascorbic acid without glucose and acetosyringone, but adding 100 mg/l carbenicillin and 5 mg/l PPT or 1.5 mg/l Bialaphos as a selection medium. The selection procedure will be the same as that used in Treatment 1. After the well-growing callus is recovered, the callus is moved to PHI-E. The calli are then cultured on PHI-F medium under a daylight schedule of 16 hrs. light (270 uE m$^{-2}$sec$^{-1}$) and 8 hrs. dark until shoots and roots develop. Each small plantlet is then transferred to a 25×150 mm tube containing PHI-F medium and grown under the same conditions for approximately another week. The plants are transplanted to pots with soil mixture in a greenhouse. Stable transformation will be confirmed by DNA analysis and herbicide resistance.

Treatment-3: Fresh sorghum immature embryos of 0.8 to 1.5 mm are isolated from sterilized immature kernels. The isolated embryos are inoculated with 10$^6$ to 10$^8$ cfu/ml Agrobacterium suspension (Agrobacterium suspended in PHI-I medium) and co-cultivated with Agrobacterium on PHI-J medium plus 10 mg/l ascorbic acid at 25° C. in the dark for about 3 days. The embryos are then subjected to a second infection step. The embryos are inoculated with 10$^8$ to 10$^9$ cfu/ml Agrobacterium suspension (Agrobacterium suspended in PHI-I medium) and co-cultivated with Agrobacterium on PHI-J medium plus 10 mg/l ascorbic acid for about an additional 4 days at 25° C. in the dark. No resting step will be applied and selection begins immediately after co-cultivation. All of the embryos are then transferred to new plates containing PHI-J medium plus 10 mg/l ascorbic acid without glucose and acetosyringone, but adding 100 mg/l carbenicillin and 5 mg/l PPT or 1.5 mg/l Bialaphos as a selection medium. The selection procedure will be the same as that used in Treatment 1. After the well-growing callus is recovered, the callus is moved to PHI-E. The calli are then cultured on PHI-F medium under a daylight schedule of 16 hrs. light (270 uE m$^{-2}$sec$^{-1}$) and 8 hrs. dark until shoots and roots develop. Each small plantlet is then transferred to a 25×150 mm tube containing PHI-F medium and grown under the same conditions for approximately another week. The plants are transplanted to pots with soil mixture in a greenhouse. Stable transformation will be confirmed by DNA analysis and herbicide resistance.

Treatment-4: Fresh sorghum immature embryos of 0.8 to 1.5 mm are isolated from sterilized immature kernels. The isolated embryos are cultured on PHI-J medium plus 10 mg/l ascorbic acid at 25° C. for about 7 days. The precultured embryos are inoculated with 10$^9$ cfu/ml Agrobacterium suspension (Agrobacterium suspended in PHI-I medium) and co-cultivated on PHI-J medium plus 10 mg/l ascorbic acid at 25° C. in the dark for about 7 days. No resting step will be applied and selection begins immediately after co-cultivation. All of the embryos are then transferred to new plates containing PHI-J medium plus 10 mg/l ascorbic acid without glucose and acetosyringone, but adding 100 mg/l carbenicillin and 5 mg/l PPT or 1.5 mg/l Bialaphos as a selection medium. The selection procedure will be the same as that used in Treatment 1. After the well-growing callus is recovered, the callus is moved to PHI-E. The calli are then cultured on PHI-F medium under a daylight schedule of 16 hrs. light (270 uE m$^{-2}$sec$^{-1}$) and 8 hrs. dark until shoots and roots develop. Each small plantlet is then transferred to a 25×150 mm tube containing PHI-F medium and grown under the same conditions for approximately another week. The plants are transplanted to pots with soil mixture in a greenhouse. Stable transformation will be confirmed by DNA analysis and herbicide resistance.

Treatment-5: Fresh sorghum immature embryos of 0.8 to 1.5 mm are isolated from sterilized immature kernels. The isolated embryos are cultured on PHI-J medium plus 10 mg/l ascorbic acid at 25° C. for about 7 days. The precultured embryos are bombarded with gold or tungsten particles at 200 mm Hg to increase wounding. The bombarded embryos are inoculated with 10$^9$ cfu/ml Agrobacterium suspension (Agrobacterium suspended in PHI-I medium) immediately following bombardment and co-cultivated on PHI-J medium plus 10 mg/l ascorbic acid at 25° C. in the dark for about 7 days. No resting step will be applied and selection begins immediately after co-cultivation. All of the embryos are then transferred to new plates containing PHI-J medium plus 10 mg/l ascorbic acid without glucose and acetosyringone, but adding 100 mg/l carbenicillin and 5 mg/l PPT or 1.5 mg/l Bialaphos as a selection medium. The selection procedure will be the same as that used in Treatment 1. After the well-growing callus is recovered, the callus is moved to PHI-E. The calli are then cultured on PHI-F medium under a daylight schedule of 16 hrs. light (270 uE m$^{-2}$sec$^{-1}$) and 8 hrs. dark until shoots and roots develop. Each small plantlet is then transferred to a 25×150 mm tube containing PHI-F medium and grown under the same conditions for approximately another week. The plants are transplanted to pots with soil mixture in a greenhouse. Stable transformation will be confirmed by DNA analysis and herbicide resistance.

Treatment-6: To provide a negative control, fresh sorghum immature embryos of 0.8 to 1.5 mm are isolated from sterilized immature kernels. No infection or co-cultivation with Agrobacterium is used. The embryos are cultured on PHI-J plus 10 mg/l ascorbic acid without glucose and acetosyringone at 25° C. in the dark, but adding 100 mg/l carbenicillin and 5 mg/l PPT or 1.5 mg/l Bialaphos. No callus growth is expected.

Analysis of Results:

The regenerated T0 plants are assayed by Southern or PCR methods to confirm stable transformation. Additionally, the plants are painted with the herbicide Liberty to verify BAR gene expression. The T1 generation is analyzed to confirm transmission of the transgene. The following comparison will determine the specificity of this technology.

The results of the treatments will provide guidance on the factors which are important for transformation of the sorghum lines being tested. Similar methods can be used to efficiently transform any sorghum line. A comparison of the data from: Treatments 1 and 2 will indicate the importance of the resting step on transformation; Treatments 2 and 3 indicate whether a second infection increases transformation; Treatments 2 and 4 indicate the importance of the pre-culture of the isolated embryos; and Treatments 4 and 5 indicate whether bombardment can improve transformation efficiency with Agrobacterium.

Using the methods of the invention any sorghum line can be stably transformed. The transformed plants of the invention are an improvement over the transformed sorghum plants produced by bombardment. In contrast to the plants produced by bombardment, the plants of the invention contain transferred nucleic acid which has not undergone any major rearrangements. Furthermore, the transferred nucleic acid integrates into the genome in low copy numbers, usually as a single copy.

Example 4

Transformation Results

P898012 was used as a model line to test the treatment conditions set forth in Example 3. Embryos were harvested, cultured and transformed as described in Treatments 1–6, respectively. The transformation frequency for each treatment is set forth in Table 2.

TABLE 2

Transformation Results

| Treatment | Condition | Expt. # | Embryo # | # Event | Frequency |
|---|---|---|---|---|---|
| 1 | Fresh embryo with Agroinfection (1 × $10^9$ cfu/ml), co-cultivation for 3 days & resting for 4 days. | G-1 | 155 | 2 | 1.3% |
|  |  | G-2 | 128 | 1 | 0.8% |
|  |  | G-3 | 123 | 1 | 0.8% |
|  |  | G-4 | 123 | 2 | 1.6% |
|  |  | G-5 | 162 | 1 | 0.6% |
|  |  | G-6 | 148 | 1 | 0.7% |
|  |  | G-7 | 122 | 2 | 1.6% |
|  |  | G-8 | 130 | 1 | 0.8% |
|  |  | G-9 | 76 | 5 | 6.6% |
|  |  | G-10 | 51 | 2 | 3.9% |
|  |  | G-11 | 144 | 1 | 0.7% |
|  |  | G-12 | 30 | 2 | 6.7% |
|  |  | Total | 1392 | 21 | 1.5% (0.6–6.6%) |
| 2 | Fresh embryo with Agroinvection (1 × $10^9$ cfu/ml), co-cultivation for 7 days & no resting | G-1 | 88 | 1 | 1.1% |
|  |  | G-2 | 104 | 1 | 1.0% |
|  |  | G-3 | 90 | 2 | 2.2% |
|  |  | G-4 | 95 | 1 | 1.1% |
|  |  | G-5 | 133 | 1 | 0.8% |
|  |  | G-6 | 47 | 2 | 4.3% |
|  |  | G-7 | 53 | 1 | 1.9% |
|  |  | G-8 | 117 | 1 | 0.9% |
|  |  | G-9 | 108 | 2 | 1.9% |
|  |  | G-10 | 118 | 2 | 1.7% |
|  |  | G-11 | 229 | 2 | 0.9% |
|  |  | G-12 | 121 | 2 | 1.7% |
|  |  | G-13 | 96 | 1 | 1.0% |
|  |  | Total | 1,399 | 19 | 1.4% (0.8–4.3%) |
| 3 | Fresh embryo 1st infection (0.001 × $10^9$–0.1 × $10^9$ cfu/ml) and 2nd infection (0.5 × $10^9$–1 × $10^9$ cfu/ml) at the 3rd day of co-cultivation, additional 4 days for 2nd co-cultivation and no resting | G-1 | 76 | 0 | 0% |
|  |  | G-2 | 84 | 0 | 0% |
|  |  | G-3 | 100 | 0 | 0% |
|  |  | G-4 | 84 | 1 | 1.2% |
|  |  | G-5 | 85 | 0 | 0% |
|  |  | G-6 | 93 | 0 | 0% |
|  |  | G-7 | 100 | 0 | 0% |
|  |  | Total | 622 | 1 | 0.2% (0–1.2%) |
| 4 | Pre-culture 3–7 days and then Agroinfection (1 × $10^9$ cfu/ml), co-cultivation for 7 days and no resting | G-1 | 48 | 1 | 2.1% |
|  |  | G-2 | 70 | 1 | 1.4% |
|  |  | G-3 | 92 | 1 | 1.1% |
|  |  | G-4 | 110 | 3 | 2.7% |
|  |  | G-5 | 227 | 1 | 0.4% |
|  |  | G-6 | 94 | 1 | 1.1% |
|  |  | Total | 641 | 8 | 1.2% (0.4–2.7%) |
| 5 | Pre-culture 5–7 days, bombarding & Agroinfection (1 × $10^9$ cfu/ml), co-cultivation for 7 days and no resting | G-1 | 119 | 0 | 0% |
|  |  | G-2 | 120 | 0 | 0% |
|  |  | G-3 | 103 | 1 | 1.0% |
|  |  | G-4 | 100 | 0 | 0% |
|  |  | Total | 442 | 1 | 0.2% (0–1.0%) |
| 6 | no Agroinfection control | G-1 | 21 | 0 | 0% |
|  |  | G-2 | 10 | 0 | 0% |
|  |  | G-3 | 20 | 0 | 0% |
|  |  | G-4 | 53 | 0 | 0% |
|  |  | G-5 | 17 | 0 | 0% |
|  |  | G-6 | 35 | 0 | 0% |
|  |  | G-7 | 46 | 0 | 0% |
|  |  | G-8 | 36 | 0 | 0% |
|  |  | G-9 | 30 | 0 | 0% |
|  |  | G-10 | 28 | 0 | 0% |
|  |  | Total | 296 | 0 | 0% |

* G = greenhouse embryos

The data showed that for P89012, stable transgenic events were readily produced with treatment-1, treatment-2 and treatment-4. In treatment-1, 21 stable events were generated from 1,392 embryos in 12 experiments and the average transformation frequency was 1.5%, ranging from 0.6–6.6%. In treatment-2, 19 events were generated from 1,399 embryos in 13 experiments and the average frequency was 1.4%, ranging from 0.8–4.3%. In treatment-4, 8 events were generated from 641 embryos in 6 experiments and the average frequency was 1.2%, ranging from 0.4–2.7%.

However, in experimental practice, treatment-2 is preferred because it is a simplified procedure. One does not have to move the embryos in different media.

In treatment-4, a pre-culture period of 3 days, 4 days, 5 days and 7 days was tested. The transformation frequencies were in the same range in these different days pre-culture treatment. The data from these different days pre-culture were pooled together to represent the results of treatment-4.

One event was produced from 442 embryos in treatment-5. Bombardment (treatment-5) actually reduced the transformation frequency from 1.2% (treatment-4) to 0.2% (treatment-5). Pre-culture for 5 days and 7 days were tested in this treatment and the data were pooled together because no obvious difference could be observed in these two pre-culture conditions.

No event was produced in the non-Agrbacterium infection control (treatment-6).

Example 5

Further Optimizations

Using P898012, further optimization of the transformation conditions was tested. Some conditions such as the use of an antioxidant and the source of sorghum embryos were tested. The results indicate that an antioxidant and source of embryos (sorghum plant growth conditions) played a role in sorghum transformation efficiency.

Antioxidant:

Antioxidants have been used in Agrobacterium-mediated transformations in at least one plant in the art. Those results indicated that antioxidants were very critical for Agrobacterium-mediated transformation of grape (*Vitis vinifera* L.) (Avihai Peri et al. (1996) *Nature Biotechnology* 14:624–628).

To test the role of antioxidants in sorghum, the protocol of treatment 2 was followed with the addition of 1% PVPP (polyvinylpolypyrrolidone) in the co-cultivation medium (710P).

The results are provided in Table 3.

TABLE 3

| Treatment | PVPP | Total Empryos | Stable Events | Frequency |
|---|---|---|---|---|
| 2 | NO | 1,399 | 19 | 1.4% |
| 2 | 1% in PHI-T | 501 | 12 | 2.4% |

Example 6

Transformation of PH391

The preferred conditions of Example 4 were repeated using field grown sorghum PH391. PH391 is an elite line in the sorghum breeding program. The transformation methodologies developed using model line P898012 were also tested in PH391 to verify the common application of these methologies in general sorghum transformation. The results are given in Table 4.

TABLE 4

| Treatment | Condition | Plant # | Embryo # | Stable Event # | Frequency (%) |
|---|---|---|---|---|---|
| 1 | Fresh embryo with Agroinfection (0.5 × $10^9$ cfu/ml), co-cultivation for 3 days and resting for 4 days, | T-1 | 115 | 9 | 7.8% |
| | | T-2 | 90 | 2 | 2.2% |
| | | Total (2) | 205 | 11 | 5.4% |
| 2 | Fresh embryo with Agroinfection (0.5 × $10^9$ cfu/ml), co-cultivation for 7 days (1% PVPP) & no resting, | T-1 | 20 | 4 | 20.0% |
| | | T-2 | 60 | 1 | 1.7% |
| | | Total (2) | 85 | 5 | 6.3% |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A method for transforming sorghum with a nucleotide sequence of interest, said method comprising the steps of:

contacting an immature embryo from a sorghum plant with an Agrobacterium comprising a vector which comprises said nucleotide sequence, wherein said nucleotide sequence comprises at least an expression cassette comprising a gene which confers resistance to a selection agent;

co-cultivating said immature embryo with said Agrobacterium;

culturing said immature embryo in a medium comprising an antibiotic capable of inhibiting the growth of said Agrobacterium and said selection agent;

regenerating transformed sorghum plants.

2. The method of claim 1, further comprising the step of culturing embryos for several days prior to the co-cultivation step.

3. The method of claim 1, wherein the vector is a super-binary vector.

4. The method of claim 3, wherein the concentration of Agrobacterium ranges from about $1 \times 10^3$ cfu/ml to about $1.5 \times 10^9$ cfu/ml.

5. The method of claim 1, wherein the contacting step takes place in a liquid suspension.

6. The method of claim 1, wherein the co-cultivation step takes place on a solid medium.

7. The method of claim 1 additionally comprising a resting step after the co-cultivation step.

8. The method of claim 7, wherein said resting step comprises culturing the tissue in a medium comprising an antibiotic capable of inhibiting the growth of Agrobacterium.

9. The method of claim 1, wherein said antibiotic is selected from the group consisting of Cefotaxime, timetin, vancomycin, and carbenicillin.

10. The method of claim 9, wherein said antibiotic is carbenicillin.

11. The method of claim 10, wherein the concentration of carbenicillin in the selection step is about 50 mg/l to about 200 mg/l.

12. The method of claim 1, wherein said gene which confers resistance to a selection agent is selected from the group consisting of bar, pat, ALS, HPH, HYG, EPSP, and Hm1.

13. The method of claim 12, wherein said gene which confers resistance to a selection agent is bar.

14. The method of claim 1, wherein said expression cassette comprises a second gene of interest.

15. A method for transforming sorghum with a nucleotide sequence, said method comprising the steps of:

contacting an immature embryo from a sorghum plant with an Agrobacterium comprising a super-binary vector which comprises said nucleotide sequence, wherein said nucleotide sequence comprises at least an expression cassette comprising a gene which confers resistance to a selection agent;

co-cultivating said immature embryo with said Agrobacterium;

culturing said immature embryo in a medium comprising an antibiotic capable of inhibiting the growth of said Agrobacterium and said selection agent;

regenerating transformed sorghum plants.

16. The method of claim 15, further comprising the step of culturing embryos for several days prior to the co-cultivation step.

17. The method of claim 15, wherein said super-binary vector is selected from PHP11264 and PHP10525.

18. The method of claim 17, wherein the concentration of Agrobacterium ranges from about $1 \times 10^3$ cfu/ml to about $1.5 \times 10^9$ cfu/ml.

19. The method of claim 15, wherein the contacting step takes place in a liquid suspension.

20. The method of claim 15, wherein the co-cultivation step takes place on a solid medium.

21. The method of claim 15, additionally comprising a resting step after the co-cultivation step.

22. The method of claim 21, wherein said resting step comprises culturing the tissue in a medium comprising an antibiotic capable of inhibiting the growth of Agrobacterium.

23. The method of claim 15, wherein said antibiotic is selected from the group consisting of Cefotaxime, timetin, vancomycin, and carbenicillin.

24. The method of claim 23, wherein said antibiotic is carbenicillin.

25. The method of claim 24, wherein the concentration of carbenicillin in the selection step is about 50 mg/l to about 200 mg/l.

26. The method of claim 15, wherein said gene which confers resistance to a selection agent is selected from the group consisting of bar, pat, ALS, HPH, HYG, EPSP, and Hm1.

27. The method of claim 26, wherein said gene which confers resistance to a selection agent is bar.

28. The method of claim 15, wherein said expression cassette comprises a second gene of interest.

* * * * *